(12) United States Patent
Sahin et al.

(10) Patent No.: US 9,737,566 B2
(45) Date of Patent: Aug. 22, 2017

(54) CHEMOTHERAPEUTIC DRUG COMBINATION

(71) Applicant: YEDITEPE ÜNIVERSITESI, Istanbul (TR)

(72) Inventors: Fikrettin Sahin, Istanbul (TR); Aysegül Dogan, Istanbul (TR); Selami Demirci, Istanbul (TR); Nese Basak, Malatya (TR); Bulent Dede, Isparta (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 0 days.

(21) Appl. No.: 15/114,854

(22) PCT Filed: Jan. 14, 2015

(86) PCT No.: PCT/TR2015/000025
§ 371 (c)(1),
(2) Date: Jul. 28, 2016

(87) PCT Pub. No.: WO2015/116012
PCT Pub. Date: Aug. 6, 2015

(65) Prior Publication Data
US 2016/0346325 A1 Dec. 1, 2016

(30) Foreign Application Priority Data

Jan. 30, 2014 (TR) ............... a 2014 01073

(51) Int. Cl.
| | | |
|---|---|---|
| A61K 39/395 | (2006.01) | |
| A61K 33/34 | (2006.01) | |
| A61K 31/15 | (2006.01) | |
| A61K 31/77 | (2006.01) | |
| A61K 33/32 | (2006.01) | |
| C08L 71/02 | (2006.01) | |

(52) U.S. Cl.
CPC .............. *A61K 33/34* (2013.01); *A61K 31/15* (2013.01); *A61K 31/77* (2013.01); *A61K 33/32* (2013.01); *C08L 71/02* (2013.01)

(58) Field of Classification Search
None
See application file for complete search history.

(56) References Cited

U.S. PATENT DOCUMENTS

| 7,390,832 B2 | 6/2008 | Rokita et al. |
| 2013/0065864 A1 | 3/2013 | Habtemariam et al. |

FOREIGN PATENT DOCUMENTS

| CN | 101342142 A * | 1/2009 |
| EP | 2407164 A1 | 1/2012 |

OTHER PUBLICATIONS

Zhang et al. "Induction of tumor cell apoptosis by taurine Schiff base copper complex is associated the with inhibition of proteasomal activity". International Journal of Molecular Medicine, 22(5), 677-682. 2008.*

Bal et al. "Cobalt(II) and Manganese (II) complexes of Novel Schiff Bases, Synthesis, Characterization, and Thermal, Antimicrobial, Electronic, and catalytic Features", Advances in Chemistry, vol. 2014. 1-8.*

Aboul-Fadl, T., Radwan, A. A., Attic, M. I., Al-Dhfyan, A., and Abdel-Aziz, H. A. (2012). Schiff bases of indoline-2, 3-dione °satin) with potential antiproliferative activity. Chemistry Central Journal, 6(1), 49.

Basu, S., Ganguly, A., Chakraborty, P., Sen, R., Banerjee, K., Chatterjee, M., and Choudhuri, S. K. (2011). Targeting the mitochondrial pathway to induce apoptosis necrosis through ROS by a newly developed Schiff's base to overcome MDR in cancer. Biochimie.

Brydøy, M., Fosså, S. D., Dahl, O., and Bjøro, T. (2007), Gonadal dysfunction and fertility problems in cancer survivors. Acta Oncologica, 46(4), 480-489.

Chan, M. H. E., Crouse, K. A., Tahir, M. I. M., Rosli, R., Umar-Tsafe, N., and Cowley, A. R. (2008). Synthesis and characterization of cobalt (II), nickel (II), copper (II), zinc (II) and cadmium (II) complexes of benzyl< i> N</i>-[1-(thiophen-2-yl) ethytidene] hydrazine carbodithioate and benzyl< i> N</i>-[1-(thiophen-3-yl) ethylidene] hydrazine carbodithioate} nickel (II). Polyhedron, 27(4), 1141-1149.

Exner, A. A., Krupka, T. M., Scherrer, K., and Teets, J. M. (2005). Enhancement of carboplatin toxicity by Pluronic block copolymers. Journal of controlled release, 106(1), 188-197.

Gelderblom, H., Verweij, J., Nooter, K., and Sparreboom, A. (2001). Cremophor EL: the drawbacks and advantages of vehicle selection for drug formulaton.European Journal of Cancer, 37(13), 1590-1598.

Li, C., Yu, D., Inoue, T., Yang, D. J., Milas, L., Hunter, N. R., and Wallace, S. (1996). Synthesis and evaluation of water-soluble polyethylene glycol-paclitaxel conjugate as a paclitaxel prodrug. Anti-cancer drugs, 7(6), 642.

Padhye, S., Yang, H., Jamadar, A., Cui, Q. C., Chavan, D., Dominiak, K., and Sarkar, F. H. (2009). New difluoro Knoevenagel condensates of curcumin, their Schiff bases and copper complexes as proteasome inhibitors and apoptosis inducers in cancer cells. Pharmaceutical research, 26(8), 1874-1880.

Ravoof, T. B., Crouse, K. A., Tahir, M. I. M., Cowley, A. R., and Ali, M. A. (2007). Synthesis, characterization and bioactivity of mixed-ligand Cu (II) complexes containing Schiff bases derived from < i> S</i>-benzyldithiocarbazate and saccharinate ligand and the X-ray crystal structure of the copper-saccharinate complex containing< i> S</i>-benzyl-β-< i> N</i>-(acetylpyrid-2-yl) methylenedithiocarbazate. Polyhedron, 26(6), 1159-1165.

(Continued)

*Primary Examiner* — Susan Tran
(74) *Attorney, Agent, or Firm* — Gokalp Bayramoglu

(57) ABSTRACT

The present invention relates to a chemotherapeutic drug combination containing heterodinuclear Cu (II)-Mn(II) complex. The objective of the present invention is to provide a drug combination, which will be actively used in chemotherapy, is anticarcinogenic and has no side effects, facilitates penetration into the cell, shows selectivity only for cancer cells and does not harm healthy cells, and is not toxic for the tissues and organs in the body, and which can prepared easily and provides a definitive and fast treatment.

4 Claims, 2 Drawing Sheets

(56) References Cited

OTHER PUBLICATIONS

Ren, S., Wang, R., Komatsu, K., Bonaz-Krause, P., Zyrianov, Y., McKenna, C. E., and Lien, E. J. (2002). Synthesis, biological evaluation, and quantitative structure-activity relationship analysis of new Schiff bases of hydroxysemicarbazide as potential antitumor agents. Journal of medicinal chemistry, 45(2), 410-419.

Uckun, F. M., Zheng, Y., Cetkovic-Cvrlje, M., Vassilev, A., Lisowski, E., Waurzyniak, B., Chen, C. L. (2002). In Vivo Pharmacokinetic Features, Toxicity Profile, and Chemosensitizing Activity of α-Cyano-β-hydroxy-β-methyl-N-(2, 5-dibromophenyl) propenamide (LFM-A13), a Novel Antileukemic Agent Targeting Bruton's Tyrosine Kinase. Clinical cancer research, 8(5), 1224-1233.

Yalvac, M.E., Ramazanoglu, M., Gumru, O.Z., Sahin, F., Palotás, A., Rizvanov, A.A. (2009). Comparison and optimisation of transfection of human dental follicle cells, a novel source of stem cells, with different chemical methods and electro-poration. Neurochemical research, 34(7), 1272-1277.

Young, J. G., Green, N. K., Mautner, V., Searle, P. F., Young, L. S., James, N. D. (2007). Combining gene and immunotherapy for prostate cancer. Prostate cancer and Prostate cancer and prostatic diseases, 11(2), 187-193.

Zhang, X., Bi, C., Fan, Y., Cui, Q., Chen, D., Xiao, Y., and Dou, Q. R. (2008). Induction of tumor cell apoptosis by taurine Schiff base copper complex is associated with the inhibition of proteasomal activity. International journal of molecular medicine, 22(5), 677-682.

Dede, B., Karipcin, F., and Cengiz, M. (2009). Novel homo-and hetero-nuclear copper (II) complexes of tetradentate Schiff bases: synthesis, characterization, solvent-extraction and catalase-like activity studies. Journal of hazardous materials, 163(2), 1148-1156.

Chakraborty A et al: "Evaluation of a Schiff base copper complex compound as potent anticancer molecule with multiple targets of action", European Journal of Pharmacology, Elsevier Science, NL, vol. 647, No. 1-3, (Nov. 25, 2010), pp. 1-12, XP027374237, ISSN: 0014-2999 [retrieved on Aug. 24, 2010] cited in the application p. 11, col. 1, pagraph 1.

* cited by examiner

CHEMOTHERAPEUTIC DRUG COMBINATION

TECHNICAL FIELD

The present invention relates to a chemotherapeutic drug combination containing heterodimic tear Cu(II)-Mn(II) complex.

BACKGROUND OF THE INVENTION

One or more cytotoxic and antineoplastic drugs are systemically used in chemotherapy treatment for cancer treatment. Today there is a wide variety of chemotherapeutic drugs used in treatment of various cancers. Paclitaxel, doxonibicin and cisplatin are some of the most known of these drugs. Although they have many side effects, antineoplastic effects thereof are determined in many studies. The chemotherapeutic drugs, which are cited in the literature and are used, do not exhibit full effect and additionally have a considerable number of side effects. Particularly cells which divide rapidly such as hair follicle or intestinal mucosa cells are affected by chemotherapeutic drugs. Suppression of immune system and the gastrointestinal problems constitute the main side effects that are observed. Hair loss and infertility are determined as the other main problems that are encountered during cancer treatment (Bryday et al., 2007). Hence a demand has emerged to develop new alternative treatment methods and chemical agents, which will minimize or eradicate the side effects occurring in the said treatment. Development of suitable pharmaceutical formulations cannot be possible only by eliminating the side effects. In the studies conducted, it is determined that molecules, whose cytotoxicity is defined and proved in in vitro and in vivo conditions should be prepared in the form of highly soluble formulations which maintain their stability (Gelderblom et al., 2001). It is known that paclitaxel as a proved chemotherapeutic drug in the literature has problems of poor solubility and stability (Li et al., 1996).

Compounds, which are formed as a result of condensation of aldehydes and ketones with primary amines under suitable reaction conditions, and which include C=N in their structure, are defined as Schiff base. It was demonstrated with the previous studies that Schiff bases, which can be used as catalysts in oxidation and reduction reactions, have anti-fungal and anti-bacterial effects and can be used as anti-microbial agents. One of the most important targets of the pharmacological studies is to develop new molecular agents which have anti-tumoral activity. This encourages inorganic and organometallic chemistry to develop new metal-containing drugs that may be effective against cancer.

There are studies in the literature showing usage of different Schiff bases against cancer. Organotin, which is a Schiff base derivative, has been used against seven different tumor cell lines, namely A498, EVSA-T, H226, IGROV, M19 MEL, MCF7 and MDR, and successful results have been obtained (Tushar et al. 2009). In another study, it was shown by using a liver cell line (Hep-G2) that Schiff base derivatives stop DNA synthesis by specifically inhibiting topoisomerase II without showing any mutagenic activity. Similarly, in another study using MCF7 which is the breast cancer cell line, Schiff base derivative showed significant amount of cytotoxic activity when compared with doxorubicin. It was also determined on neuroblastoma (SH-SY5Y) cells that. Schiff complexes disturb redox balance and thereby cause breaks in DNA and exhibit cytotoxic activity. These complexes can carry the metal residing in its structure via the cell membrane by targeting mitochondria and nucleus and cause oxidative stress and thus apoptosis. It was determined that copper containing Schiff base complexes activate apoptotic pathways thereby showing anticancer activity. In the previous studies with human breast cancer (MDA-MB-13 leukemia (Jurkat T), human colon cancer cells (HCT116) and pancreatic cancer (BxPC3) cells, it has been demonstrated that Schiff base copper complexes serve as a proteasome inhibitor and lead cancer cell death by causing accumulation of apoptotic proteins such as Bax (Zhang et al., 2008; Padhye et al.; 2009). Schiff base complexes exerted selectively anticarcinogenic activity on chronic myelogenic leukemia K562 cells when compared to MCF-12A cells which is the healthy cell line. (Aboul-Fadl et al.; 2012). In another study conducted with L1210 murine leukemia cells, Schiff base derivative has been more effective than hydroxyurea which is used in treatment of melanoma, leukemia and ovarian cancer (Ren et al.; 2002). It was determined in the previous studies that Schiff bases cause caspase-3 dependent apoptose in MDR (Multi Drug Resistance) cells by increasing the ROS (reactive oxygen species) content (Basu et al., 2011). Different Schiff base derivatives that were synthesized have been tried on many cancer cells such as cervical cancer (HeLa), leukemia (HL-60), cervical cancer (Caov-3), colon cancer (HT-29) and lung cancer (MRC-5) due to their antineoplastic activities (Ravoof et al., 2007; Chan et al., 2008).

Pluronic block copolymers Which are also known as poloxamers can be used for drug, growth factor and gene transport. The polymers are comprised of hydrophilic polyethyleneoxide and hydrophobic polypropyleneoxide units. Different numbers of ethylene oxide and propylene oxide monomers enable to obtain different pluronics. Each plutonic copolymer has different, biological effects. Since they are capable of forming micelle in liquid solutions, they can easily transport the drugs into the cells.

Studies related to Schiff base have also been conducted in the studies of state of the art applications Dede, B., Karipcin, F., and Cengiz, M. (2009).

The United States patent document no. US20130065864 discloses a combination containing iridium and/or rhodium for use in cancer treatment.

The European patent document no. EP2407164A1 discloses an anti-cancer complex which contains Cu-II compound and which can be in the form of a complex with different components.

The United States patent document no. U.S. Pat. No. 7,390,832B2 discloses a copper-based complex for treating tumors.

SUMMARY OF THE INVENTION

The objective of the present invention is t' wide a drug combination that can be used actively in chemotherapy.

Another objective of the present invention is to provide an anticarcinogenic drug combination with no side effects.

A further objective of the present invention is to provide drug combination which facilitates penetration into the cells.

Another objective of the present invention is to provide a drug combination which shows selectivity only for cancer cells and does not harm healthy cells.

Another objective of the present invention is to provide a drug combination which is not toxic for the tissues and organs in the body.

A farther objective of the present invention is to provide a drug combination which can be easily prepared.

Another objective of the present invention is to provide a drug combination which enables a definitive and fast treatment.

A further objective of the present invention is to provide a drug combination which does not cause known chemotherapeutic side effects such as gastrointestinal system disorders such as mouth ulcers, taste changes, irritation in the inner lining of the bowel, diarrhea, appetite problems and nausea; anemia, hemorrhage, fall in blood counts, fatigue, hair loss, nervous system disorders, pain, reproductive system disorders, disorders that may occur on the skin and nails.

BRIEF DESCRIPTION OF THE DRAWINGS

The "Chemotherapeutic drug combination" developed to fulfill the objectives of the present invention is shown in the accompanying figures wherein.

Figure 1:
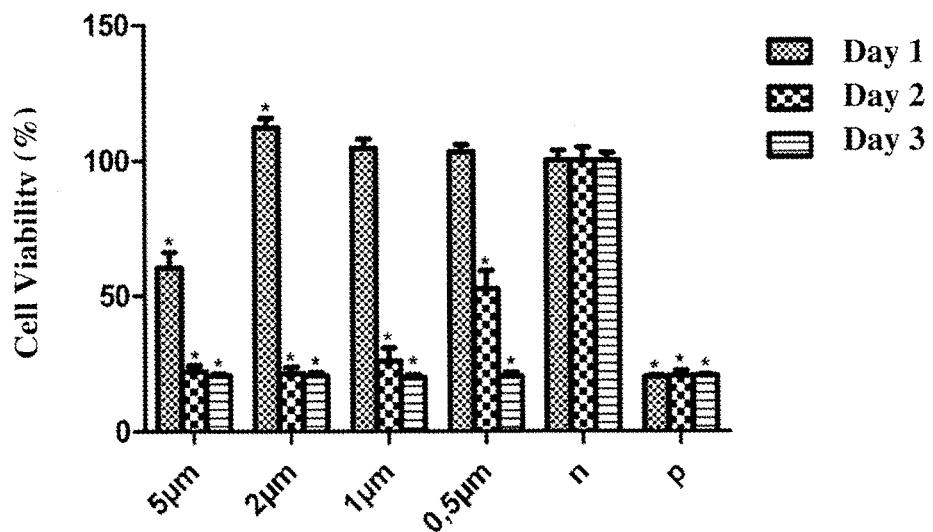
FIG. 1 is the representation of the toxicity of the drug combination on TRAMP cells (*P<0.05; n: negative control, p=positive control).

In the scope of the present invention, a new chemotherapeutic drug is developed by combining a chemical molecule, which is Schiff-base derivative, with a block copolymer, which specifically recognizes cancer cells and speeds up penetration of the drug. In the drug combination, while the polymeric substance serves as a supporting molecule, Schiff-base is used as the active molecule group. In the drug combination that is prepared, pluronic P85 polymer, which facilitates penetration of the drug into the cell, is used. Thus, by enabling the penetration of the drug selectively only for cancer cells, it is enabled to obtain toxic effect without harming the healthy cells.

DETAILED DESCRIPTION OF THE INVENTION

Preparation of the Chemotherapeutic Drug Combination

Polynuclear Schiff (heterodinuclear Cu (II)-Mn(II) complex) base complex is used as the chemical molecule in preparation of the chemotherapeutic drug formulation. This complex was used in combination with pluronics. The combination was prepared at different concentrations in in vitro and in vivo conditions and applied in the experiments. The Schiff base solution and pluronic solution, which were prepared separately for the experimental studies, were used in combination.

In Preparation of the Combination

Schiff base was dissolved in DMSO (1 mg/ml) main stock solution and a homogenous solution was obtained. Since Schiff base is photosensitive, the processes including Schiff base were performed in a dark environment.

The prepared Schiff base solution was used either in PBS or cell culture medium or by injecting to animals at concentrations in the range of 0.0001-10 μg ml for in vitro conditions and at concentrations in the range of 0.001 mg/kg-10 mg/kg for in vivo conditions.

The pluronic which is the polymer solution is weighed at a ratio of 10% and the main stock solution was prepared and used. This polymer solution was incubated at 4° C. overnight and was used after being filtered through a 0.2 μm filter. Final concentration of the pluronic was determined as 0.05%. This concentration ma vary between 0.0001 and 2%.

Finally, Schiff base derivative and pluronic were mixed and allowed to rest at room temperature for 15 minutes. Then medium was added thereon and it was made ready for use. The drug combination of the present invention will be denoted with the code CMSB1422113 in commercial applications. When injecting to animals, it was made up to a total volume with PBS and prepared in an injectable form.

In the drug combination, Pluronic is selected from at least one of F68, F127, P106, P407, P85, P123.

Characterization Studies

Determining Cell Toxicity

Toxic effect of the prepared chemicals was determined by analyzing cell viability using the MTS method (Yalvac et al., 2009). The drug combination was prepared at concentrations of 5 μM, 2 μM, 1 μM, 0.5 μM and was applied on the cancer cells which were counted and seeded on 96-well culture plates (5000 cells/Well). Toxicity response was determined by measuring cell viability for 3 days, formazan crystals are formed in MTS substance applied cells as a result of mitochondrial dehydrogenase enzyme activity as an indicator of cell viability. The color change was evaluated by measuring absorbance by ELISA device. The obtained values were analyzed using Microsoft Office Excel database.

In Vivo Toxicology Analyses

After the in vitro experiments were completed, in vivo toxicology analyses were performed in order to observe the effects of the drug formulation in the system of a living organism system. Acute toxicological analyses were performed as previously stated in the literature (Uckun et al, 2002). The prepared formulation was first tried on prostate cancer. Toxicology studies were conducted on C57 mice which are used in experiments. Four different doses of 0.1 mg/kg, 0.5 mg/kg and 1 mg/kg were administered intraperitoneally to male C57 mice. 7 days later the mice were sacrificed (acute toxicology). Blood parameters and histopathological analyses were completed.

Forming In Vivo Tumor Model

Visible prostate cancer tumor tissue was formed in the animals at the dorsal region by modifying the protocol which was described previously in the literature (Young et 2007). 20×10$^6$ TRAMP cells were administered to male C57 mice subcutaneously. Tumor formation process was monitored. At the end of an approximately 44 day process, the tumors became visible.

Inhibiting In Vivo Tumor Formation

In order to observe the effects of the developed drug formulation on tumor formation, 20×10$^6$ TRAMP cells were subcutaneously injected to 20 kg weighing C57 mice to the dorsal region near the tail. After one week following the injection, 0.5 mg/kg Schiff base derivative and 500 mg/kg plutonic were combined and injected to the animals which were separated as the experimental group. Saline was administered to the control group animals. At the end of 13 injections when death began in the control group animals, the experiment was terminated. Tumor photographs were taken and the pathological examination was completed.

Statistical Analysis

The results obtained were statistically evaluated by one-way analysis of variance (ANOVA) using GraphPad Prism 5 software. The difference between the groups was determined by Tukey's test and $p \leq 0.05$ was considered statistically significant.

Experimental Results

In order to show the toxic effects of the drug combination of the present invention, toxicology tests were performed using the cancer and healthy cell lines. TRAMP (Mouse prostate cancer cells) prostate cancer cells, whose model will be formed in animals, were used as the cancer cell line. L929 (Mouse fibroblast cells) fibroblast cells were used as the healthy cell line. The drug combination was applied on the cells at concentrations of 5 μM. 2 μM, 1 ρM, 0.5 μM and the effects were examined at the end of three day toxicology analyses. Toxic effect was started to be observed at the end of the second day at four concentrations, and after three days of analysis, a significant amount of toxicity (at the same level with the positive control) was determined when compared with the negative control group (FIG. 1).

Figure 2:
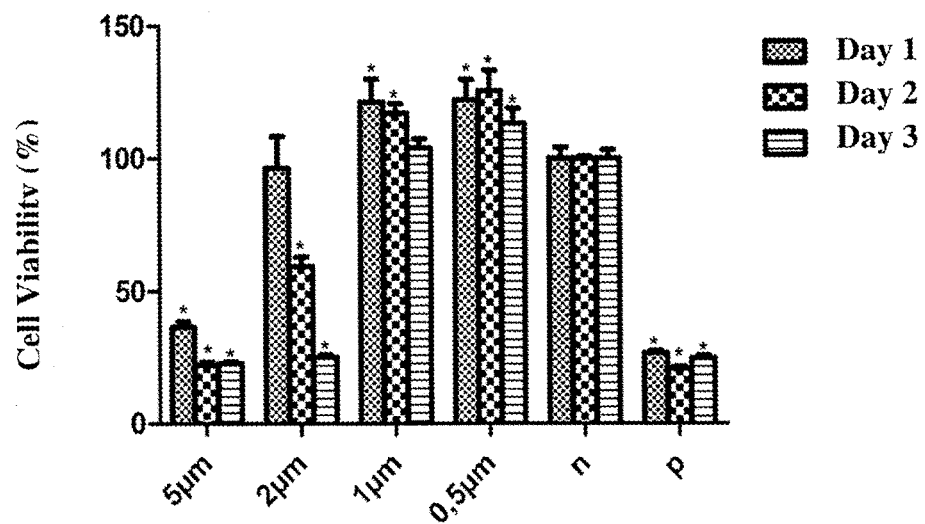
FIG. 2 is the representation of the toxicity of the drug combination on L929 cells (*P<0.05; n: negative control, p=positive control).

Fibroblast cells were used in order to determine the toxicity of the drug combination at the same concentrations on healthy cells. Toxicity was observed at the end of three days at the two highest concentrations (5 μM and 2 μM), while no toxicity was observed at the concentrations of 1 μM and 0.5 μM (FIG. 2).

The findings obtained showed that while the drug combination killed the cancer cells, it increased viability in the healthy cells. In vivo toxicology analyses were performed in order to support the findings and start in vivo studies. 0.5 mg/kg was determined to be the highest non-toxic concentration after blood parameters and enzyme analyses, (Table 1-2-3).

Figure 3:
FIG. 3 is the toxicity observed after application of 1 mg/kg of the drug combination. (A) Liver tissue focal necrosis. (B) Kidney tissue lymphatic infiltration, (C) Hydrophobic degeneration in kidney tubular tissue, 1ing/kg drug combination.

After necroscopy, tissue and organ weights of the animals were measured and analyses were performed to find out Whether there were any anomalies. Tissue and organ samples were pathologically examined and while no toxicity was found at concentrations of 0.1 mg/kg, 0.25 mg/kg, 0.5 mg/kg, a low level of toxicity was observed at the concentration of 1 mg/kg. Focal necrosis was observed in the liver tissue and hydrophobic degeneration in hepatocytes. Lymphatic infiltration was observed in the kidneys and hydrophobic degeneration in the kidney tubules (FIG. 3). 0.5 mg/kg was selected as the concentration to be applied in animal experiments after tumor formation.

TABLE 1

Blood parameter (enzyme, protein, etc.) results obtained after toxicity analysis of the drug combination at a concentration of 0.5 mg/kg.

| Parameter | G3 (0.5 mg/kg) | Control | Description |
|---|---|---|---|
| AST (U/L) | 255 | 176 | The enzyme is a significant indicator of liver function. |
| ALT (U/L) | 101 | 100 | The enzyme is a significant indicator of liver function |
| CK (U/L) | 804 | 775 | The enzyme is a significant indicator of renal function |
| Amylase (U/L) | 415 | 383 | The enzyme is a significant indicator of pancreatic function. |
| Bilirubin (mg/dl) | 0.06 | 0.05 | The enzyme is a significant indicator of liver damage. |
| Albumin (mg/dl) | 2.70 | 2.43 | The enzyme is a significant indicator of liver damage. |
| Creatinine (mg/dl) | 0.58 | 0.48 | The enzyme is a significant indicator of renal damage. |
| Urea (mg/dl) | 45.75 | 40.50 | The enzyme is a significant indicator of renal and cardiac damage. |
| Protein (g/dl) | 6.48 | 6.33 | The enzyme is a significant indicator of renal damage. |

TABLE 2

Blood cells results obtained after toxicity analysis of the drug combination at a concentration of 0.5 mg/kg.

| Parameter | G3 (0.5 mg/kg) | Control |
|---|---|---|
| WBC | 6.97 | 7.17 |
| RBC | 7.54 | 7.89 |
| PLT | 708.75 | 709.00 |
| EOS# | 0.06 | 0.07 |
| EOS % | 0.90 | 0.80 |
| LYM# | 4.46 | 4.93 |
| LYM % | 72.11 | 73.78 |
| BAS# | 0.06 | 0.05 |
| BAS % | 0.02 | 0.02 |
| MON# | 0.44 | 0.41 |
| MON % | 4.98 | 4.73 |
| NEU# | 1.34 | 1.13 |
| NEU % | 21.43 | 19.00 |

TABLE 3

Blood parameter results obtained after toxicity analysis of the drug combination at a concentration of 0.5 mg/kg.

| Parameter | G3 (0.5 mg/kg) | Control | Description |
|---|---|---|---|
| Hgb (g/dL) | 14.88 | 15.05 | is an indicator of the hemoglobin values in blood. |
| MCV (fL) | 51.15 | 51.80 | is an indicator of the average size of the oxygen carrying cells. |

TABLE 3-continued

Blood parameter results obtained after toxicity analysis of the drug combination at a concentration of 0.5 mg/kg.

| Parameter | G3 (0.5 mg/kg) | Control | Description |
|---|---|---|---|
| MCH (pg) | 19.48 | 19.58 | is an indicator of the hemoglobin content in erythrocytes. |
| MCHC (g/dL) | 39.23 | 38.38 | is an indicator of the average hemoglobin concentration in erythrocytes. |
| RDW-SD (fL) | 29.43 | 27.93 | is an indicator of the erythrocyte distribution width. |
| MPV (fL) | 5.95 | 5.98 | is an indicator of platelet size. |
| PDW | 14.93 | 14.75 | is an indicator of the platelet distribution width. |
| HCT % | 44.03 | 51.75 | is a measure of the hemoglobin and erythrocyte content. |
| RDW-CV % | 14.28 | 14.23 | is an indicator of the erythrocyte distribution width. |
| PCT % | 0.45 | 0.44 | is an indicator of the platelet ratio in blood. |

Prostate tumor was formed experimentally on C57 mice in order to reproduce the clinical picture. In the pilot study, tumor formation was induced by using different numbers of cells.

Figure 4:
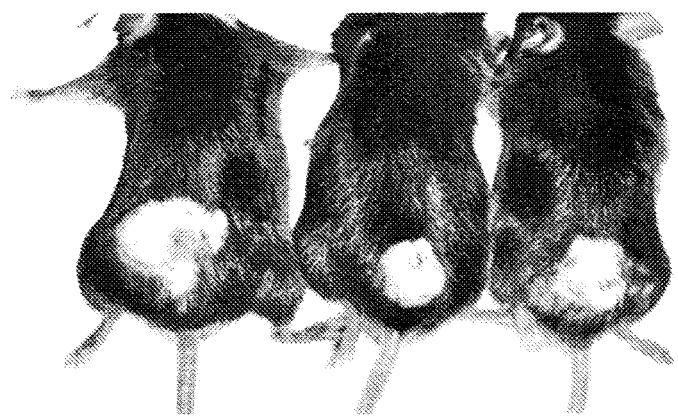
FIG. 4 is the representation of the tumor formation at the dorsum after 20×10$^6$ TRAMP cell injection.

Following the experiment, tumors were formed by subcutaneously injecting twenty million cells to the dorsal region within a period of 30-40 days (FIG. 4).

After the tumor formation was successfully completed, experiments in the scope of the treatment were started. Following one week after the tumor cell was injected, the drug combination prepared by using Schiff base at a dose of 0.5 mg/kg, was intraperitoneally administered to the animals once every four days. At the end of 13 injections, when death began in the control (physiological saline application) group animals, the experiment, was terminated. The tumors were weighed and pathological analyses were conducted (Table 4-5).

Figure 5:
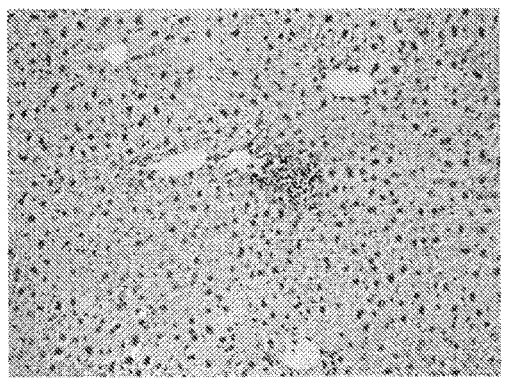
FIG. 5 is the hepatic portal field focus of inflammation. It is the toxicity observed in the liver following the thug administration.

Prostatic adenocarcinoma formation was analyzed by using Gleason scoring. In the group to which the drug was administered, no toxicological effect was encountered except a mild congestion in the spleen. A small number of lymphocytic cells were detected around the liver central vein (FIG. 5).

TABLE 4

Results of pathological examination of tumor tissue of control group animals

| Group (control) | Tumor | Gleason Score |
|---|---|---|
| C1 | Prostatic adenocarcinoma | Gleason score 9 (4 + 5) |
| C2 | Prostatic adenocarcinoma | Gleason score 9 (4 + 5) solid tumor-diffuse necrosis |
| C3 | Prostatic adenocarcinoma | Gleason score 9 (5 + 4) solid tumor, necrotic and a plurality of apoptotic cells |
| C4 | Prostatic adenocarcinoma | Gleason score 9 (4 + 5), small tumor. necrotic areas and apoptotic cells |
| C5 | Prostatic adenocarcinoma | Gleason score 10 (5 + 5) |
| C6 | Tumor tissue was monitored in a limited area. | Gleason score could not be assigned |
| C7 | Prostatic adenocarcinoma | Gleason score 10 (5 + 5) tumor solid pattern |
| C8 | Prostatic adenocarcinoma | 9 (5 + 4) solid pattern |

TABLE 5

Results of pathological examination of tumor tissue of experimental group animals

| Group (Drug Administration) | Tumor | Gleason Score |
|---|---|---|
| D1 | No tumor | |
| D2 | No tumor | |
| D3 | edematous tissue, chronic inflamation and fibrosis are present, no tumor | |
| D4 | Prostatic adenocarcinoma | Gleason score 9 (5 + 4) |
| D5 | Prostatic adenocarcinoma | Gleason score 10 (5 + 5), solid pattern tumor is present |
| D6 | No tumor | |
| D7 | No tumor | |
| D8 | Prostatic adenocarcinoma | Gleason score 10 (5 + 5) |

With the present invention, a new easily-prepared drug combination is obtained which can be actively used in chemotherapy and which is not toxic to the other tissues and organs of the body. The present invention can provide a definitive and rapid treatment by enabling the drug to penetrate the cancer cells rapidly and at a large quantity. Many drugs which are developed for chemotherapy have a great number of side effects. Problems such as gastrointestinal system disorders such as mouth ulcers, taste changes, irritation in the inner lining of the bowel, diarrhea, appetite problems and nausea, anemia, hemorrhage problems, fall in blood counts (damage on division of bone marrow cells), fatigue, hair loss, nervous system disorders, pain, reproductive system disorders, disorders occurring on the skin and nails are experienced following chemotherapy. The drug combination of the present invention is capable of eliminating these kinds of side effects.

APPLICATION OF THE INVENTION

The present invention provides a treatment for the cancer types seen in human body by reducing the side effects. The formulation developed within the scope of the invention can be effective on all cancer types particularly prostate cancer. It can be used for treatment of AIDS-related cancer types, breast cancer and derivatives thereof, gastrointestinal tract-related cancer types, endocrine and neuroendocrine cancers, eye cancer, genitourinary system cancer types, gynecological cancer types, prostate cancer and derivatives thereof, germ cell cancer, head and neck cancer, hematologic cancer and leukemia, musculoskeletal system cancers, neurological cancers, respiratory system and thoracic cancers, skin cancer, cancers of unknown origin, cancer types observed in childhood (acute lymphoblastic leukemia, acute myeloid leukemia), cancer types observed in women (breast, cervical, endometrial, ovarian, uterus, vaginal, vulval etc.)

The invention is effective in treatment and prevention of cancer types such as astrocytoma, glioma, lung cancer, hepatoma, colon cancer, osteoid cancer, pancreatic cancer skin cancer, cervical cancer, melanoma, uterine cancer, ovarian cancer, rectal cancer, gastric cancer, anal cancer, colon carcinoma, breast cancer, fallopian tube cancer, endometrial cancer, cervical cancer, vaginal cancer, Hodgkin's disease, esophageal cancer, small bowel cancer, endocrine gland cancer, thyroid cancer, parathyroid cancer, adrenal cancer, soft tissue sarcoma, urethral cancer, penial cancer, prostate cancer, urinary bladder cancer, kidney or ureter cancer, renal cell carcinoma, pelvic carcinoma, central nervous system (CNS) tumor, primary CNS lymphoma, spinal cord tumor and hypophysis adenoma.

REFERENCES

Aboul-Fadl, T., Radwan, A. A., Attia, M. I., Al-Dhfyan, A., and Abdel-Aziz, H. A. (2012). Schiff bases of indoline-2, 3-dione (isatin) with potential antiproliferative activity. *Chemistry Central Journal*, 6(1), 49.

Basu, S., Ganguly, A., Chakraborty, P., Sen, R., Banerjee, K., Chatterjee, M., and Choudhuri, S. K. (2011). Targeting the mitochondrial pathway to induce apoptosis/necrosis through ROS by a newly developed Schiff's base to overcome MDR in cancer. *Biochimie*.

Brydøy, M., Fosså, S. D., Dahl, O., and Bjøro, T. (2007). Gonadal dysfunction and fertility problems in cancer survivors. *Acta Oncologica*, 46(4), 480-489.

Chan, M. H. E., Crouse, K. A., Tahir, M. I. M., Rosli, R. Umar-Tsafe, N. and Cowley. A. R. (2008). Synthesis and characterization of cobalt (II), nickel (II), copper (II), zinc (II) and cadmium (II) complexes of benzyl<i>N</i>-[1-(thiophen-2-yl) ethylidene] hydrazine carbodithioate and benzyl<i>N>N<i>-[1-(thiophen-3-yl) ethylidene] hydrazine carbodithioate and the X-ray crystal structure of bis {benzyl<i>N</i>-[1-(thiophen-2-yl) ethylidene] hydrazine carbodithioate} nickel (II). *Polyhedron*, 27(4), 1141-1149.

Exner, A. A., Krupka, T. M., Scherrer, K., and Teets, J. M. (2005). Enhancement of carboplatin toxicity by Pluronic block copolymers. *Journal of controlled release*, 106(1). 188-197.

Gelderblom, H, Verweij, J., Nooter, K., and Sparreboom, A. (2001). Cremophor EL: the drawbacks and advantages of vehicle selection for drug formulation. *European Journal of Cancer*, 37(13), 1590-1598.

Li, C., Yu, D., Inoue, T., Yang, D. S., Milas, L., Hunter, N. R., and Wallace, S. (1996). Synthesis and evaluation of water-soluble polyethylene glycol-paclitaxel conjugate as a paclitaxel prodrug. *Anti-cancer drugs*, 7(6), 642.

Padhye, S., Yang, H., Jamadar, A., Cui, Q. C., Chavan, D., Dominiak, K. and Sarkar, F. H. (2009). New difluoro Knoevenagel condensates of curcumin, their Schiff bases and copper complexes as proteasome inhibitors and apoptosis inducers in cancer cells. *Pharmaceutical research*, 26(8), 1874-1880.

Ravoof. T. B., Crouse, K A., Tahir, M. I. M., Cowley, A. R. and Ali. M. A. (2007). Synthesis, characterization and bioactivity of mixed-ligand Cu (II) complexes containing Schiff bases derived from <i>S</i>-benzyldithiocarbazate and saccharinate ligand and the X-ray crystal structure of the copper-saccharinate complex containing<i>S</i>-benzyl-β-<i> N</i>-(acetylpyrid-2-yl) methylenedithiocarbazate. *Polyhedron,* 26(6), 1159-1165

Ren, S., Wang, R., Komatsu, K., Bonaz-Krause, P., Zyrianov, Y., McKenna, C. E. and Lien, E. J. (2002). Synthesis, biological evaluation, and quantitative structure-activity relationship analysis of new Schiff bases of hydroxysemicarbazide as potential antitumor agents. *Journal of medicinal chemistry,* 45(2), 410-419.

Uckun, F. M., Zheng, Y., Cetkovic-Cvrlje, M., Vassilev, A., Lisowski, E., Waurzyniak, B., and Chen, C. L. (2002). In Vivo Pharmacokinetic Features, Toxicity Profile, and Chemosensitizing Activity of α-Cyano-β-hydroxy-β-methyl-N-(2,5-dibromophenyl) propenamide (LFM-A13), a Novel Antileukemic Agent Targeting Bruton's Tyrosine Kinase. *Clinical cancer research,* 8(5), 1224-1231.

Yalvac, M. E., Ramazanoglu, M. Gumru, O. Z., Sahin, F., Palotás, A. and Rizvanov, A. A. (2009). Comparison and optimisation of transfection of human dental follicle cells, a novel source of stem cells, with different chemical methods and electro-poration, *Neurochemical research,* 34(7), 1272-1277.

Young, J. G. Green, N. K., Mautner, V., Searle, P. F., Young, L. S., and James, N. D. (2007), Combining gene and immunotherapy for prostate cancer. *Prostate cancer and prostatic diseases,* 11(2). 187-193, Zhang, X., Bi, C., Fan, Y., Cui, Q., Chen, D., Xiao, Y., and Dou, Q. P. (2008). Induction of tumor cell apoptosis by taurine Schiff base copper complex is associated with the inhibition of proteasomal activity. *International journal of molecular medicine.* 22(5), 677-682.

Dede, B. Karipcin, F., and Cengiz. M. (2009). Novel homo- and hetero-nuclear copper (II) complexes of tetradentate Schiff bases: synthesis, characterization, solvent-extraction and catalase-like activity studies. *Journal of hazardous materials,* 163(2). 1148-1156.

The invention claimed is:

1. A chemotherapeutic drug combination comprising a combination of a polynuclear Schiff base complex and a pluronic;
   wherein the polynuclear Schiff base complex is heterodinuclear Cu (II)-Mn(I) complex;
   wherein the pluronic is P85;
   wherein the combination of the polynuclear Schiff base complex and the pluronic enables penetration of the chemotherapeutic drug combination selectively for cancer cells while increasing viability in healthy cells.

2. The chemotherapeutic drug combination according to claim 1, a concentration of the polynuclear Schiff base complex is 0.5 mg/Kg or less.

3. The chemotherapeutic drug combination according to claim 1, a concentration of the polynuclear Schiff base complex is 0.5 mg/Kg.

4. A chemotherapeutic drug combination, consisting of a combination of a polynuclear Schiff base complex and a pluronic;
   wherein the polynuclear Schiff base complex is heterodinuclear Cu (II)-Mn(I) complex;
   wherein the pluronic is selected from at least one of F68, P106, P407, P85, and P123.

* * * * *